United States Patent [19]

Sullivan

[11] Patent Number: 5,419,914
[45] Date of Patent: May 30, 1995

[54] PHOSPHOLIPID ANALOGUE VESICLE

[75] Inventor: Séan M. Sullivan, Pasadena, Calif.

[73] Assignee: Vestar, Inc., San Dimas, Calif.

[21] Appl. No.: 295,184

[22] Filed: Aug. 24, 1994

Related U.S. Application Data

[63] Continuation of Ser. No. 890,345, May 21, 1992, abandoned, which is a continuation of Ser. No. 594,378, Oct. 9, 1990, abandoned.

[51] Int. Cl.$^6$ .............................................. A61K 9/127
[52] U.S. Cl. .................................. 424/450; 428/402.2
[58] Field of Search ...................... 424/450; 428/402.2; 264/4.1, 4.3; 436/829

[56] References Cited

U.S. PATENT DOCUMENTS

| | | | |
|---|---|---|---|
| 4,429,008 | 1/1984 | Martin et al. | 424/450 X |
| 4,751,219 | 6/1988 | Kempen | 424/450 X |
| 5,080,833 | 1/1992 | Ishimori | 436/518 |

FOREIGN PATENT DOCUMENTS

| | | |
|---|---|---|
| 272091 | 6/1988 | European Pat. Off. |
| WO8604232 | 7/1986 | WIPO |
| 8302069 | 6/1989 | WIPO |
| 8911270 | 11/1989 | WIPO |
| WO/8911270 | 11/1989 | WIPO |

OTHER PUBLICATIONS

Machy et al. Proc. Natl. Acad. Sci. (1988 85:8027–8031).
Karin Renneisen, et al. "Inhibition of Expression of Human Immunodeficiency Virus-1 in Vitro . . . ", J. Biol. Chem. (1990) 265(27):16337–16342.
Patrick Machy, et al. "Gene Transfer from Targeted Liposomes to Specific Lymphoid Cells by Electroporation", Proc. Natl. Acad. Sci., (1988) 85:8027–8031.
PCT Written Opinion (PCT/US 91/07549) dated 07 Oct. 1992, the remarks concerning section IV (sheets 1–2) This is a written opinion relatd to the PCT application corresponding to the present application.
PCT International Preliminary Report (PCT/US 91/07549) dated 11 Dec. 1992, comments 2–5 (sheets 1–2). This is a report relted to the PCT application corresponding to the present application.
Australian Industrial Property Organization Patent Office, Examiner's first report, dated 23 Sep. 1993. This is a report related to the Australian application corresponding to the present application.
"Lipid", Patent Abstracts of Japan, vol. 13, No. 303, p. 896 (Toshiba Corp.) Mar. 23, 1989.
"Production of Lipid Microsphere Bound to Physiologically Active Protein", Patent Abstracts of Japan, vol. 13, No. 61, C567, (Yutaka Mizushima) Oct. 20, 1988.
"Reagent for Immunoassay", Patent Abstracts of Japan, vol. 13, No. 303, p. 896 (Toshiba Corp.) Mar. 23, 1989.
"Reconstituted Viral Envelopes-'Trojan Horses' for Drug Delivery and Gene Therapy", Blumenthal et al., Tibtech, vol. 9, pp. 41–45, Feb. 1991.
Form PCT/ISA/220 mailed Mar. 24, 1992 for application PCT/US91/07549.
Leonetti et al., Proc. Natl. Acad. Sci. 87, 2448–2451 (1990).
Milhaud et al., Biochim. Biophys. Acta 987, 15–20 (1989).
Wang et al., Biochemistry 28, 9508–9514 (1989).
Pinnaduwage et al., Biochim. Biophys. Acta 985, 33–37 (1989).
Ceccoli et al., J. Invest. Derm. 93, 190–194 (1989).
Dhananjaya et al., J. Virol. Methods 19, 131–140 (1988).
Stavridis et al., Exp. Cell Res. 164, 568–572 (1986).
Fraley, Plant Molec. Biol. 2, 5–14 (1983).

*Primary Examiner*—Gollamudi S. Kishore
*Attorney, Agent, or Firm*—Adam Cochran; George A. Gilbert

[57] ABSTRACT

Delivery vehicle formulations comprising active agents encapsulated within microparticles which include a succinimidyl moiety extending externally from a lipid molecule therein are capable of the cytoplasmic or nuclear cell delivery of intact encapsulated active agents.

16 Claims, No Drawings

PHOSPHOLIPID ANALOGUE VESICLE

This is a continuation of application Ser. No. 07/890,345, filed on May 21, 1992, now abandoned, which is a continuation of Ser. No. 07/594,378, filed Oct. 9, 1990, now abandoned.

FIELD OF THE INVENTION

This invention relates generally to the fields of biochemistry and medicine, and more particularly to delivery vehicle formulations comprising an active agent encapsulated within liposomes that include a superficial transport promoter which facilitates intact cytoplasmic uptake of the agent by cells.

BACKGROUND OF THE INVENTION

Microscopic lipid delivery vehicles such as liposomes may be employed to convey therapeutic and diagnostic agents to specific locations in a body. Such delivery vehicles encapsulate the active ingredient, which is thus isolated from degradative effect of body fluids and capable of having a desired effect at particular sites in the body. For this reason, it has long been thought that these vehicles would be appropriate for the therapeutic delivery of oligonucleotides to cells in vivo, since oligos such as DNA and RNA are quickly degraded in body fluids before the therapeutic target cell is reached.

Liposomes are vesicles composed of lipid bilayers completely surrounding an internal aqueous space. They are usually made up of phospholipids or other amphipathic molecules either in pure form or in combination with other molecules such as sterols, i.e., cholesterol. Methods for the preparation and use of liposomes are well known in the art. Such vehicles have been viewed as a potential mechanism for delivering agents to cells to enter, and affect, natural cell growth and other metabolic functions.

In cell metabolism, substances which are normally taken up by cells from the intercellular medium (e.g., vitamins, carbohydrates, amino and nucleic acids, and certain other molecules) cross the cell membrane through natural transporter proteins (i.e., ports) which are specific for the particular substance transported. If a substance does enter the cell through such a natural port, it enters the metabolic pathways of the cell intact. However, substances which cross the cell membrane for which a transporter protein does not exist, such as phospholipid delivery vehicles, go directly to an organelle within the cell called a lysosome. The lysosome is a vacuole which comprises a digestive mechanism for degrading nonspecific nutrients or internal cell products into their primary form for use by the cell.

The liposome delivery of water soluble drugs to cells has often relied upon liposome phagocytosis for transport across the cell membrane, which results in liposome delivery to the lysosome. The lipids are degraded releasing the entrapped drug. For a cytoplasmically or nucleus active drug, the drug must diffuse from this intracellular organelle without degradation to the site of therapeutic action. Certain drugs possess the necessary characteristics to achieve this goal, such as methotrexate or 5-fluoro-oratate, which have a weakly acidic group which upon protonation makes the drug hydrophobic, thus allowing it to pass relatively intact across the lysosomal membrane without loss of therapeutic effect. However, many agents are incapable of escaping lysosomal degradation, and the use of phagocytic transport of liposomal drugs is limited to these specific types of molecules. Oligonucleotides, such as DNA and RNA sequences, require cytoplasmic delivery to be effective and since they are degraded by the lysosome following phagocytic transport by lipid particles.

To attenuate this natural process, liposome formulations have been designed to fuse to internal cellular membranes at low pH and deliver DNA to the cytoplasm of cells. There are several requirements in that the liposome must remain attached to the membrane surface after phagocytosis, and the lipids must be composed of a lipid which forms a fusion competent configuration and which is stabilized by a weakly acidic lipid component. These two requirements once again limit the application of this technology for the extra-lysosomal delivery of agents to cells. First, not all liposome formulations remain attached to the membrane following endocytosis. Second, the fusion competent lipid formulation utilizes lipids which are not ideal for pharmaceutical manufacture, for stable shelf life or for serum stability.

Thus, it has been a desideratum to have a lipid delivery vehicle which would provide for the cytoplasmic delivery of an entrapped active agent in the essential absence of lysosomal degradation, and particularly if such formulations possessed the qualities of shelf life and serum stability. As used herein, the cytoplasmic delivery of an entrapped active agent in the essential absence of lysosomal degradation means a delivery wherein an amount of the active agent sufficient to affect cell function escapes lysosomal degradation and enters the cytoplasm.

SUMMARY OF THE INVENTION

The invention comprises a lipid particle including a succinimidyl moiety, preferably in the form of a N-ethylsuccinimidylthiol (NEST) moiety, extending from the surface of the particle in the absence of an extending ligand conjugate. The succinimidyl moiety is attached to a phospholipid molecule to form a succinimidyl phospholipid analogue, preferably in the form of a NEST-lipid entity and most preferably in the form of a N-(N-ethylsuccinimidylthio)phosphatidylethanolamine (NESTPE) moiety, specifically N-(N-ethylsuccinimidylthio)distearoylphosphatidylethanolamine (NEST-DSPE). At least one such phospholipid analogue is included in the outer phospholipid layer of the lipid particle with the succinimidyl moiety extending therefrom, to form a phospholipid analogue particle, which is capable of permitting the encapsulated contents of the lipid particle (e.g., a liposome) to enter the cell cytoplasmically in the essential absence of lysosomal degradation. Active agents which may be encapsulated in the lipid particles of the invention, and delivered intact to the cytoplasm, include lysosomal sensitive therapeutics (such as cytosine arabinosine) proteins and peptides, nucleic acids, oligonucleotides, genes, plasmids and other lysosomal sensitive agents.

The liposome of the invention is prepared by forming a liposome containing a lipid with an extending, deprotected sulfhydryl group, which is then reacted with a maleimide moiety to form the extending succinimidyl moiety.

DETAILED DESCRIPTION

A wide variety of lipid particles may include a succinimidyl phospholipid analogue of the invention to form delivery vesicles which are capable of the intact intracellular transport of the encapsulated contents. For example, other phospholipid delivery vehicles, such as disclosed in the Vestar, Inc. patent publication EP0272091 (the counterpart of U.S. Ser. No. 942,093 filed 15 Dec. 1986), may be employed. These vehicles are composed of a single encapsulating phospholipid membrane associated with an amphiphile-associated substrate. However, the lipid particles are preferably comprised of phospholipids and most preferably are liposomes.

Phospholipids are amphipathic molecules which are the primary constituents of cell membranes. Typical phospholipid hydrophilic groups include phosphatidylcholine and phosphatidylethanolamine moieties, while typical hydrophobic groups include a variety of saturated and unsaturated fatty acid moieties. Mixture of a phospholipid in water causes spontaneous organization of the phospholipid molecules into a variety of characteristic phases depending on the conditions used. These include bilayer structures in which the hydrophilic groups of the phospholipids interact at the exterior of the bilayer with water, while the hydrophobic groups interact with similar groups on adjacent molecules in the interior of the bilayer. Such bilayer structures can be quite stable and form the principal basis for cell membranes.

Phospholipid bilayer structures can also be formed into closed spherical shell-like structures which are called phospholipid vesicles or liposomes. The membrane bilayers in these structures typically encapsulate an aqueous volume, and form a permeability barrier between the encapsulated volume and the exterior solution. Phospholipids dispersed in aqueous solution spontaneously form bilayers with the hydrocarbon tails directed inward and the polar headgroups outward to interact with water. Simple agitation of the mixture usually produces multilamellar vesicles (MLVs), structures with many bilayers in an onion-like form having diameters of 1–10 μm (1000–10,000 nm). Sonication of these structures, or other methods known in the art, leads to formation of unilamellar vesicles (UVs) having an average diameter of about 30–300 nm. However, the range of 50 to 100 nm is considered to be optimal from the standpoint of, e.g., maximal circulation time in vivo. The actual equilibrium diameter is largely determined by the nature of the phospholipid used and the extent of incorporation of other lipids such as cholesterol. Standard methods for the formation of liposomes are known in the art, for example, methods for the commercial production of liposomes are described in U.S. Pat. No. 4,753,788 to Ronald C. Gamble and U.S. Pat. No. 4,935,171 to Kevin R. Bracken.

Either as MLVs or UVs, liposomes have proven valuable as vehicles for drug delivery in animals and in humans. Active drugs, including small hydrophilic molecules and polypeptides, can be trapped in the aqueous core of the liposome, while hydrophobic substances can be dissolved in the liposome membrane. The liposome structure can be readily injected and form the basis for both sustained release and drug delivery to specific cell types, or parts of the body. MLVs, primarily because they are relatively large, are usually rapidly taken up by the reticuloendothelial system (the liver and spleen). The invention typically utilizes vesicles which remain in the circulatory system for hours and break down after internalization by the target cell. For these requirements the formulations preferably utilize UVs having a diameter of less than 200 nm, preferably less than 100 nm. Preferred liposome compositions include various mole ratios of distearoylphosphatidylcholine (DSPC) and dipalmitoylphosphatidylcholine (DPPC) and cholesterol, and include the extending succinimidyl moiety, in the absence of extending ligand conjugates such as hormones or other proteins or peptides which extend from the lipid particle, e.g., for the purpose of inducing a metabolic response in a target cell upon the binding of the ligand conjugate to its receptor. An example of this type of hormone extending from a liposome is set forth in patent publication PCT WO 89/11270, a counterpart of U.S. application Ser. No. 07/353,250, now abandoned.

The vesicle delivery vehicles described herein are preferably liposomal structures capable of incorporation, by encapsulation, of an active agent useful for the treatment or diagnosis of a mammalian disease or physiological condition, in a manner suitable for administration to the mammalian body. Unilamellar liposomes having a diameter of less than 200 nm are preferred, although MLVs or other lipid particles such as micelles, polymeric microspheres or the single encapsulating phospholipid membrane particles containing the amphiphile-associated substrate disclosed in EP0272091 may be employed.

The succinimidyl moiety of the invention has the formula

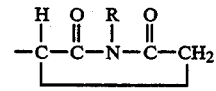

in which R is H, propyl, ethyl or methyl, and preferably ethyl.

The NEST moiety has the formula

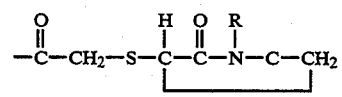

in which R is H, propyl, ethyl or methyl, and preferably ethyl.

In the example which follows, a phosphatidylethanolamine (distearoylphosphatidylethanolamine (DSPE)) is attached to an acetylthio group by the addition of succinimidylacetylthioacetate (SATA) to form a phosphatidylethanolaminoacetylthioacetate (PE-ATA) moiety, specifically distearoylphosphatidylethanolaminoacetylthioacetate (DSPE-ATA). Liposomes are then formed consisting of DPPC/Chol/DSPE-ATA, that is, liposomes consisting of DPPC/Chol/DSPE with an ATA group extending externally from the surface thereof. After liposome formation, the -ATA moiety is deacetylated by addition of either hydroxylamine or ammonium hydroxide, and the free sulfhydryl of the -ATA is then reacted with N-ethylmaleimide to form the succinimidyl moiety on the DSPE, e.g., the NEST-DSPE. With the lipophilic portion of this phospholipid contained in the bilayer membrane, the succinimidyl moiety extended from the surface of the liposome.

Alternative lipids such as dilauroyl-PE, dimyristoyl-PE, dipentadecanoyl-PE, dipalmitoyl-PE, distearoyl-PE, dipetroselinoyl-PE, dioleoyl-PE, dielaidoyl-PE, dilinoleoyl-PE, dilinolenoyl-PE, 1-palmitoyl-2-oleoyl-PE, egg-PE, plant(soy bean)-PE, bacterial (*E. coli*)-PE, heart-PE, liver-PE and brain-PE will undergo a similar reaction with SATA or other reagents to form succinimidyl containing phospholipid analogues useful in the invention.

Succinimidylacetylthiopropionate (SATP) can be substituted for succinimidylacetylthioacetate. Alternatively, liposomes containing a PE can be prepared, and 2-iminothiolane is then added along with N-ethylmaleimide to yield a coupled succinimidyl group extending from the liposome surface.

The succinimide can also be attached to other lipids such as cholesterol by the incorporation of thiocholesterol into the liposome membrane. Addition of N-ethylmaleimide will result in the formation of the succinimidylthiol moiety attached to cholesterol and extending from the liposome surface. Alternatively, aminomannose cholesterol will be derivatised with either SATA, or SATP or as in the above proposed reaction with iminothiolane. The derivatized cholesterol would then be incorporated into the liposome bilayer, and deprotection of the sulfhydryl group followed by the addition of a maleimide will yield the succinimidyl moiety attached to the liposome surface.

SYNTHESIS OF DSPE-ATA

DSPE-ATA is synthesized by a reaction which generates a modified phosphatidylethanolamine having an acetylthioester group on the ethanolamine moiety. For example, a five-fold molar excess of SATA is added to DSPE in a round bottom flask. Typically, 125 mg SATA is added to 75 mg of DSPE. 15 ml of $CHCl_3$: MeOH (1:1) is then added, followed by 100-135 $\mu$l of triethylamine. The flask is then flushed with nitrogen, sealed, and the reaction carried on for two hours at room temperature with stirring. The progress of the reaction is monitored by thin layer chromatography in $CHCl_3$: MeOH (7:3). The absence of a Ninhydrin positive, and the presence of a PMA positive spot having an Rf of 0.57 indicates the presence of DSPE-ATA. Some of this compound may oxidize to the disulfide (PE-ATTA-PE), which has an Rf of about 0.37. It should be noted that SATA is quite labile and cannot be stored for prolonged periods. The material obtained is then evaporated to dryness and resuspended in 1.0 ml of $CHCl_3$:MeOH (1:1), and 15 ml of acetonitrile is added to the dry material. This solution is held at $-20°$ C. for about 60 minutes to precipitate DSPE-ATA. The precipitate is collected by filtration on a sintered glass filter and washed with acetonitrile. The washed DSPE-ATA is again dissolved by the addition of 1:1 $CHCl_3$: MeOH and collected in a second filter flask, transferred to a preweighed flask and evaporated. The yield at this point has been between 80 and 84%.

During preparation, all steps should be conducted as quickly as possible to minimize oxidation. Separation of oxidized DSPE-ATA from unoxidized DSPE-ATA is accomplished by preparative thin layer chromatography, such as on a Kieselgel 60 plate obtained from EM Science. Aluminum backed silica gel (no fluorescent indicator) plates are used with $CHCl_3$: MeOH (7:3) as the mobile phase. DSPE-ATA is located by $I_2$ staining a strip cut from the end of the plate. The area containing DSPE-ATA is then cut out. The strips of $SiO_3$-coated aluminum are further cut up and extracted over a 30 minute period in 1:1 $CHCl_3$: MeOH. The DSPE-ATA is concentrated to dryness, dissolved in 1:1 $CHCl_3$: MeOH and dispensed into vials. Each vial is flushed with nitrogen and stored at $-20°$ C. For preparations greater than the quantities described above, a column chromatograph procedure has been developed. Specifically, sample is applied in $CHCl_3$ to a silica gel column which is also equilibrated with $CHCl_3$. The column is then washed with $CHCl_3$. A buffer head comprised of $CHCl_3$/ethylacetate is applied to the column. The volume should be one-third of the column bed volume. A buffer reservoir is fitted to the column containing methanol. The elution is initiated by dropwise addition of methanol to the chloroform/ethylacetate buffer head and the elute is collected in fractions. The yield from the column is approximately 50%.

PRODUCTION OF LIPOSOMES

Lipid solutions of DPPC/cholesterol (CHOL)/DSPE-ATA (49/25/27) and (64.5/33/2.5) in chloroform were prepared. The chloroform was evaporated under a stream of nitrogen to yield lipid films. The films were vacuum desiccated overnight to remove residual organic solvent. These films were either hydrated in 0.4 ml of 50 mM calcein, 10 mM phosphate buffer, pH 7.4 (for the fluorescense microscopy) or phosphoate buffered saline containing the respective deoxyoligonucleotides, described infra, at a concentration of 5 mg/ml. The lipid suspensions were brought through three freeze and thaw cycles using liquid nitrogen and thawing at 65° C. to facilitate homogeneous distribution of the active agent among the lamellae of the thus formed MLVs. The MLV were reduced in size by extrusion through a 0.4 um, 0.2 $\mu$m and a 0.1 um polycarbonate filters three times per filter at 65° C. at a maximum of 800 psi to yield UVs with an average diameter of 100 nm. Each sample was extruded through a set of filters separately to avoid contamination. Argon was bubbled through the lipid suspensions to remove oxygen. The thioacetylated lipid was deacetylated by addition of 30 $\mu$l of 0.5M hydroxylamine, 0.5M HEPES, 0.025M EDTA to 2.5 $\mu$mol of lipid. The suspensions were incubated at room temp for 30 min. The byproducts were removed by a sephadex G-25 spin column and the lipid suspensions were allowed to stand for 2.5 hours at room temp. N-ethylmaleimide was added to the liposomes in a mol/mol excess of ten to one with respect to the thiolated lipid and incubated overnight at 4° C. The byproducts were removed by a biogel A5M gel filtration column. The lipid fractions were pooled and sterile filtered using a 0.2 polycarbonate filter.

CYTOPLASMIC DELIVERY OF ACTIVE AGENTS

These liposome preparations were added, at a concentration of 100 $\mu$M, to $1.5 \times 10^6$ human peripheral blood mononuclear cells (PBMCs) which had been cultured for three days in phytahemagglutanin (PHA). PBMCs from HIV positive infected patients were cultured to produce virus in the supernatant. This supernatant was then used to infect the PHA stimulated uninfected PBMCs. The liposomes were added 3 hours after the PBMCs were treated with the infected supernatant. Virus production was monitored by assaying the cell supernatant for HIV core protein termed gag protein or abbreviated p24. Levels of p24 were determined by a standard ELISA assay. The number of infected cells were determined by immunochemically treating fixed infected cultures with antibody to the HIV p17 and gp41 proteins followed by a secondary antibody to which an enzyme was linked. The infected cells were visualized by then incubating with a colored substrate to the enzyme followed by staining the uninfected cells.

The liposomes containing the 5'-ATTTTCAGAATTGGGTGTCG-3' DNA (having the same sequence as the DNA coding strand of viral origin, i.e., the sense DNA) reduced the production of p24 into the cell supernatant by 85% with respect to the untreated control. Immunocytochemical staining of the infected cells showed that the liposomes containing the sense sequence reduced the number of strongly positive infected cells by 50%. It was also observed that the untreated control displayed large cell aggregates whereas the liposomes containing the sense sequence showed a greatly reduced number of large cell aggregates (approximately 30% of the untreated control). The liposomal sense DNA sequence displayed cell no toxicity as assayed by cell viability.

In a second set of experiments, free DNA was compared to liposomal DNA described above using two doses and testing for breakthrough of the virus on day 5 and day 7. Samples containing 50 and 100 μM lipid were tested, which was equivalent to a concentration of 17 and 34 nM DNA. Liposomes containing the sense sequence showed 48% inhibition of p24 production at 50 μM lipid and 50% inhibition at 100 μM lipid on day 5 of infection. On day 7 the 50 μM lipid showed 28% p24 inhibition and 31% inhibition at 100 μM lipid.

Free 5'-ATTTTCAGAATTGGGTGTCG-3' (sense) yielded −8% inhibition with 17 nM DNA and 2% inhibition with 34 nM. 17% inhibition was observed for 17 nM and 13% inhibition was observed for 34 nM DNA on day 7. Empty liposomes showed no inhibition of p24 production. Furthermore, immunocytochemical staining for infected cells showed a decrease in the number of strongly positive infected cells and the number of giant cells by treatment with liposomes containing the sense DNA sequence compared to that observed for free sense or empty liposomes.

Finally, in a third set of experiments, DNA analogues of the above sequence were prepared which reduced the DNA sensitivity to nuclease degradation. These liposomes were prepared by first codissolving the DNA and lipid in chloroform at a ratio of 0.5 mg DNA to 10 μmol lipid. The solvent was evaporated forming a film on the side of the test tube, and the film was vacuum desiccated overnight to remove residual solvent. The films were hydrated in 150 mM NaCl, 10 mM phosphate buffer. The hydrated films were then brought through three freeze and thaw cycles followed by the standard extrusion protocol previously described. Analysis showed a 23% trapping efficiency.

Empty liposomes formed by this method were tested against similar liposomes containing the above-described sense sequence. Liposomes were tested at 2, 10 and 50 μM lipid and analyzed for inhibition of p24 production on day 5 and day 7. The following results were obtained for the sense liposomes containing the low, medium and high dose: on day 5: −8%, 11% and 42% of untreated control, respectively and on day 7: −6%, 28% and 60% of the untreated control. Thus, this liposome formulation was able to effectively deliver the oligonucleotide analogue as demonstrated by the sequence specific inhibition of viral replication. Due to the nature of the modification and increased trapping efficiency, the oligonucleotide analogue is embedded in the membrane as well as entrapped in the internal aqueous space. Yet, the membrane bound material did not appear to affect the liposomes ability to deliver the entrapped material.

Nonspecific inhibition was observed for the empty liposomes as well, yielding 1%, 11% and 15% of the untreated control on day 5 and −60%, 18% and 28% of the untreated control on day 7 for the low, medium and high lipid doses.

Thus, liposomal sense DNA having the NEST moiety extending from the surface enables the cytoplasmic or nuclear cell delivery of intact encapsulated active agents, and significantly reduces viral antigen production, p24 levels, and the number of infected cells.

To better understand the liposome/cell interactions, fluorescent cell labeling experiments were performed by preparing the liposomes with an entrapped self-quenching fluorophore, calcein. After a 1 hour incubation, the cells were pelleted and observed under the fluorescent microscope to score the number of cytoplasmically stained cells. Liposomes bound to the cell surface or internalized yield punctate fluorescence whereas uniform cytoplasmic staining and exclusion from the nucleus were indicative of cytoplasmic release of dye. The lipid suspension obtaining 2.5 mol % of NEST-PE at best labeled only 1% of the cells regardless if they were infected or uninfected. However, the 27 mol % NEST-PE liposomes cytoplasmically labeled 20% of the infected and 40% of the uninfected cells. Conventional liposomes yield intracellular punctate fluorescence normally indicative of intracellular vacuol localization, i.e. delivery into the lysosome.

To further characterize the liposome uptake, kinetic measurements were made using flow cytometry in which 27 mol % DSPE-ATA liposomes were prepared in 150 mM NaCl, phosphate buffer, pH 7.4 along with dipalmitoylphosphatidylglycerol/DPPC/CHOL (50/1733) liposomes in the same buffer. The liposomes were loaded with 6-carboxyfluorescein diacetate (6-CFDA) by lowering the pH to 5.0 and adding the 6-CFDA dissolved in dimethylsulfoxide (DMSO). This fluorophore is non-fluorescent in the diacetate form. Deacetylation resulting from either base hydrolysis or enzymatic hydrolysis yields the fluorescent compound 6-carboxyfluorescein. The fluorophore was found to be stably entrapped in buffer for at least 7 days and was stably entrapped in the presence of serum for 3 hours at 37° C. Both formulations of 6-CFDA labeled liposomes were incubated with 72 hour phytahemaglutanin stimulated peripheral blood mononuclear cells (PBMCs) and the kinetics of liposome uptake were followed by flow cytometry for 48 hours. The results showed that both monocytes and lymphocytes took up the 27 mol % NEST-PE liposomes better than the 50 mol % DPPG liposomes. The results also showed that the kinetics of uptake for the lymphocytes was slower and saturated later than the monocyte liposome uptake.

Shelf life stability studies for the 27 mol % NEST-DSPE liposomes showed 85% retention of 6-CFDA and also a phosphorylated nucleotide analogue when stored at 4° C. over a one week period. Incubation in serum for 3 hours showed full retention of entrapped nucleotide analogue when analyzed by gel filtration chromatography. Hence, this liposome formulation has been shown to cytoplasmically deliver an entrapped water soluble molecule into the cell cytoplasm. The formulation is composed of lipids ideal for pharmaceutical liposome manufacture and has been effective in delivery of synthetic 20 mer deoxynucleotides complementary to the HIV genome. The formulation has reasonable shelf life stability and is suitable for i.v. administration as displayed by its serum stability with respect to retention of entrapped contents. Without the extending succinimide moiety the liposomes do not permit the cytoplasmic delivery of agents to cells, but show punctate fluouresence rather than staining of the cytoplasm.

The foregoing description is intended to present the preferred embodiments that may be utilized in practicing the present invention, but it will be apparent to those skilled in the art that modifications and equivalents may be incorporated without departing from the scope and spirit of the invention.

I claim:

1. A liposome comprising cholesterol and phosphatidylethanolamine wherein the phosphatidylethanolamine comprises an N-alkylsuccinimidylthio- moiety in which the alkyl is selected from the group consisting of methyl, ethyl or propyl, said N alkylsuccinimidylthio- moiety extending from the phosphatidylethanolamine in the absence of an extending ligand conjugate.

2. The liposome of claim 1 in which the said N-alkylsuccinimidylthio- moiety is a N-ethylsuccinimidylthio- moiety.

3. The liposome of claim 1 in which said N-alkylsuccinimidylthio- moiety is a N-(N-ethylsuccinimidylthio) phosphatidylethanolamine.

4. The liposome of claim 1 in which said N-alkylsuccinimidylthio- moiety is a N-(N-ethylsuccinimidylthio) distearoylphosphatidylethanolamine.

5. A liposome comprising cholesterol and phosphatidylethanolamine wherein the phosphatidylethanolamine comprises a succinimidyl moiety extending therefrom in the absence of an extending ligand conjugate, said moiety having the formula

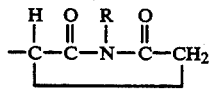

in which R is H, methyl, ethyl or propyl.

6. A method for the delivery of an active agent to the cytoplasm of a cell, comprising the administration to a host of the agent incorporated in a liposome comprising cholesterol and phosphatidylethanolamine, wherein the phosphatidylethanolamine comprises an N-alkylsuccinimidylthio- moiety in which the alkyl is selected from the group consisting of methyl, ethyl or propyl, said N alkylsuccinimidylthio- moiety extending from the phosphatidylethanolamine in the absence of an extending ligand conjugate.

7. The method of claim 6 in which said N-alkylsuccinimidylthio- moiety is a N-ethylsuccinimidylthio moiety.

8. The method of claim 6 in which said N-alkylsuccinimidylthio- moiety is a N-(N-ethylsuccinimidylthio)-phosphatidylethanolamine.

9. The method of claim 6 in which said N-alkylsuccinimidylthio- moiety is a N-(N-ethylsuccinimidylthio)-distearoylphosphatidylethanolamine.

10. The method of claim 6 in which the active agent is an oligonucleotide.

11. The method of claim 7 in which the active agent is an oligonucleotide.

12. The method of claim 8 in which the active agent is an oligonucleotide.

13. The method of claim 9 in which the active agent is an oligonucleotide.

14. A method for the delivery of an active agent to the cytoplasm of a cell, comprising the administration to a host of the agent incorporated in a liposome comprising cholesterol and phosphatidylethanolamine, wherein the phosphatidylethanolamine comprises a succinimidyl moiety extending therefrom, said moiety having the formula

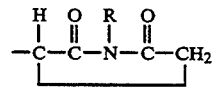

in which R is H, methyl, ethyl or propyl.

15. A liposome comprising cholesterol and phosphatidylethanolamine wherein the phosphatidylethanolamine comprises a succinimidyl moiety extending therefrom in the absence of an extending ligand conjugate, said moiety having the formula

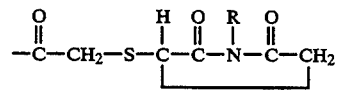

in which R is H, propyl, ethyl or methyl, and preferably ethyl.

16. A method for the delivery of an active agent to the cytoplasm of a cell, comprising the administration to a host of the agent incorporated in a liposome comprising cholesterol and phosphatidylethanolamine, wherein the phosphatidylethanolamine comprises a succinimidyl moiety extending therefrom, said moiety having the formula

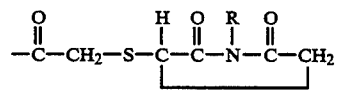

in which R is H, methyl, ethyl or propyl.

* * * * *